United States Patent [19]

Bald

[11] 4,267,444
[45] May 12, 1981

[54] DEVICE FOR EXAMINING THE DEGREE OF FILLING OF A CIGARETTE

[75] Inventor: Hubert Bald, Gevelsberg, Fed. Rep. of Germany

[73] Assignee: Maschinenfabrik Alfred Schmermund GmbH & Co., Gevelsberg, Fed. Rep. of Germany

[21] Appl. No.: 20,396

[22] Filed: Mar. 14, 1979

[30] Foreign Application Priority Data

Mar. 31, 1978 [DE] Fed. Rep. of Germany ....... 2813866

[51] Int. Cl.³ .............................................. G02B 5/16
[52] U.S. Cl. .................................... 250/227; 209/536
[58] Field of Search ............................. 209/536, 535; 250/223 R, 227

[56] References Cited

U.S. PATENT DOCUMENTS 3,473,037 10/1969 Schmermond ................... 250/223 R
3,729,636 4/1973 Merker ............................. 250/223 R
3,953,730 4/1976 Henry et al. ......................... 250/227

Primary Examiner—David C. Nelms
Assistant Examiner—Darwin R. Hostetter
Attorney, Agent, or Firm—Sughrue, Rothwell, Mion, Zinn and Macpeak

[57] ABSTRACT

A device for the examination of the degree of filling of cigarette ends is disclosed. The device has a light transmitter, a light emitting surface which radiates light into the cigarette end to be examined, and a light receiving surface which picks up the more of the light radiated in, the worse is the degree of filling. The light emitting surface and the light receiving surface are arranged in one plane at end face of the cigarette in such a manner that both bear directly against the cigarette end face and are separated by a light impervious zone from each other transversely to the axis with respect to the cigarette axis and together lie within the cigarette cross-section.

6 Claims, 5 Drawing Figures

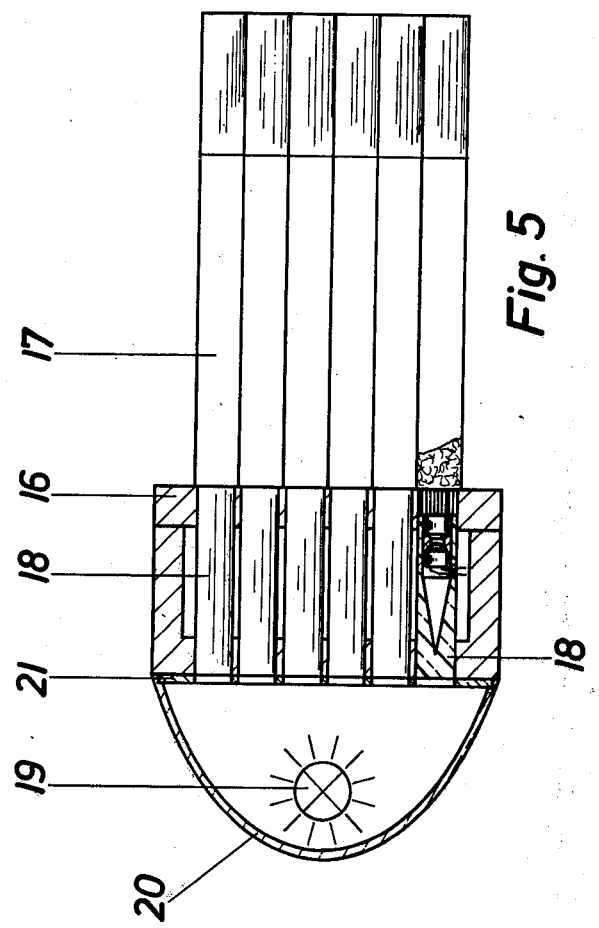
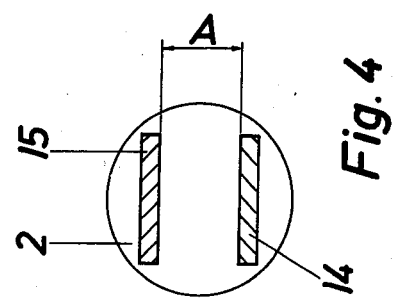
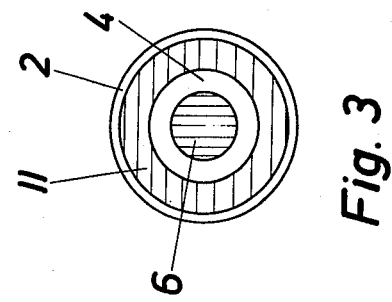

DEVICE FOR EXAMINING THE DEGREE OF FILLING OF A CIGARETTE

BACKGROUND OF THE INVENTION

The present invention relates to a device for examining the degree of filling of a zone of a cigarette.

in a disclosed device, light is radiated end-on from a certain spacing onto the cigarette end and reflected by the tobacco fibres into a light receiver which is likewise arranged end-on. The greater the reflected light, the better is the degree of filling. Reject cigarettes are therefore those in which the received light falls below a predetermined threshold value. An example of such a device is disclosed in U.K. Pat. No. 1,347,221 in which a measuring probe comprises light conducting fibres. It is an advantage of such a device that it only requires space end-on so that one can simultaneously examine several cigarettes, for example a cigarette block to be packaged, with a corresponding plurality of devices of the same type. Unfortunately, the distinction between a good and a reject cigarette is however fairly inaccurate, since on the one hand in the case of badly filled cigarette end, light reflected by fibres disposed more deeply can reach the receiver and thus falsify the measurement and, on the other hand, light is reflected past the receiver in the case of well filled cigarette ends.

The fact that slight changes of the spacing between probe and cigarette end falsify the measurement shows how small the capability of resolution is, so that complicated devices have been created for compensation of fluctuations in spacing. In this respect reference is made to DE-OS No. 26 25 001.

An improved capability of resolution can be obtained by determining the light permeability of the cigarette end. According to FIG. 5 of DE-OS No. 26 53 298, a light exit surface and light entry surface are arranged laterally and end-on, respectively, with respect to the cigarette and the better the degree of filling, the less light reaches the light receiver. In the case of this disclosure, the cigarettes must however be accessible laterally as well as end-on so that only individual examinations are possible.

SUMMARY OF THE PRESENT INVENTION

It is an object of the present invention to provide a device which requires space only end-on with respect to the cigarette to be examined, so that cigarette blocks can also be examined.

According to one aspect of the present invention there is provided a device for examining the degree of filling of an end zone of a cigarette, comprising a light source, light transmitting means having an emitting surface adapted to be disposed against an end of said cigarette to be examined and to apply light from said source thereto, light receiving means having a receiving surface co-planar with said emitting surface and spaced therefrom by a region substantially impermeable to said light, and evaluating means coupled to said receiving means and responsive to the reflectance of said end zone.

Said emitting surface may be co-axial with said receiving surface.

Said emitting surface and said receiving surface may each be rectangular and have mutually facing sides extending parallel to each other.

Said device may comprise a fibre-optical member having an end face on which said emitting surface and said receiving surface are provided.

Said device may comprise light conductive means coupling said light source optically to the respective other end face of said fibre-optical member.

According to another aspect of the present invention there is provided an apparatus for examining the degree of filling of respective end zone of each of a plurality of cigarettes, comprising a plurality of examining devices, a housing for said devices, and a common light source for said devices, each device comprising light transmitting means having an emitting surface adapted to be disposed against an end of a respective such cigarette to be examined and to apply light from said source thereto, light receiving means having a receiving surface coplanar with said emitting surface and spaced therefrom by a region substantially impermeable to said light, and evaluating means coupled to said receiving means and responsive to the reflectance of said end zone.

BRIEF DESCRIPTION OF THE DRAWINGS

Embodiments of the present invention will now be more particularly described by way of example and with reference to the accompanying drawings in which:

FIG. 3 shows an elevation of the embodiment shown in FIG. 1 in the direction of the arrow III in FIG. 2, FIG. 4 shows a similar elevation to that shown in FIG. 3 but of another embodiment of the present invention, and FIG. 5 shows a plan view of an apparatus comprising several devices embodying the present invention.

DESCRIPTION OF THE PREFERRED EMBODIMENTS

Figure 1:
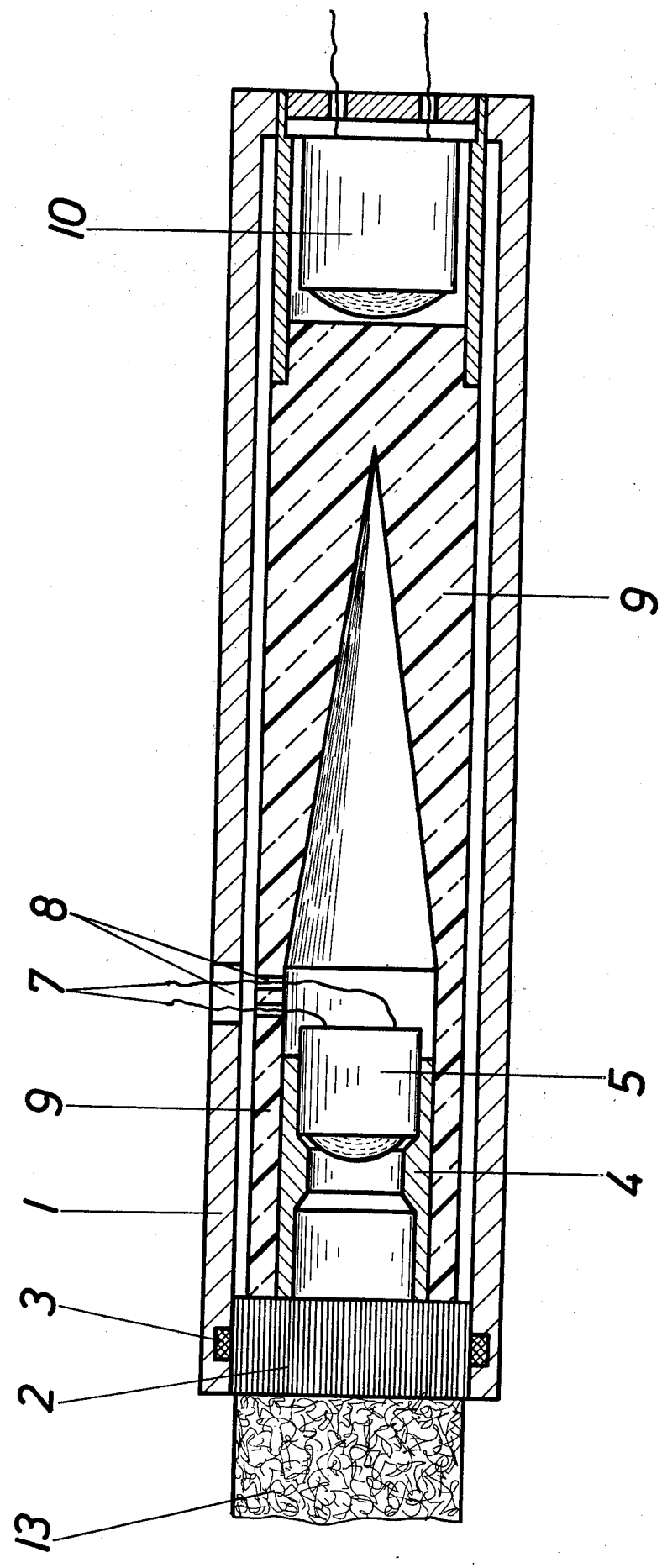
FIG. 1 shows a section through an embodiment of the present invention.
Figure 2:
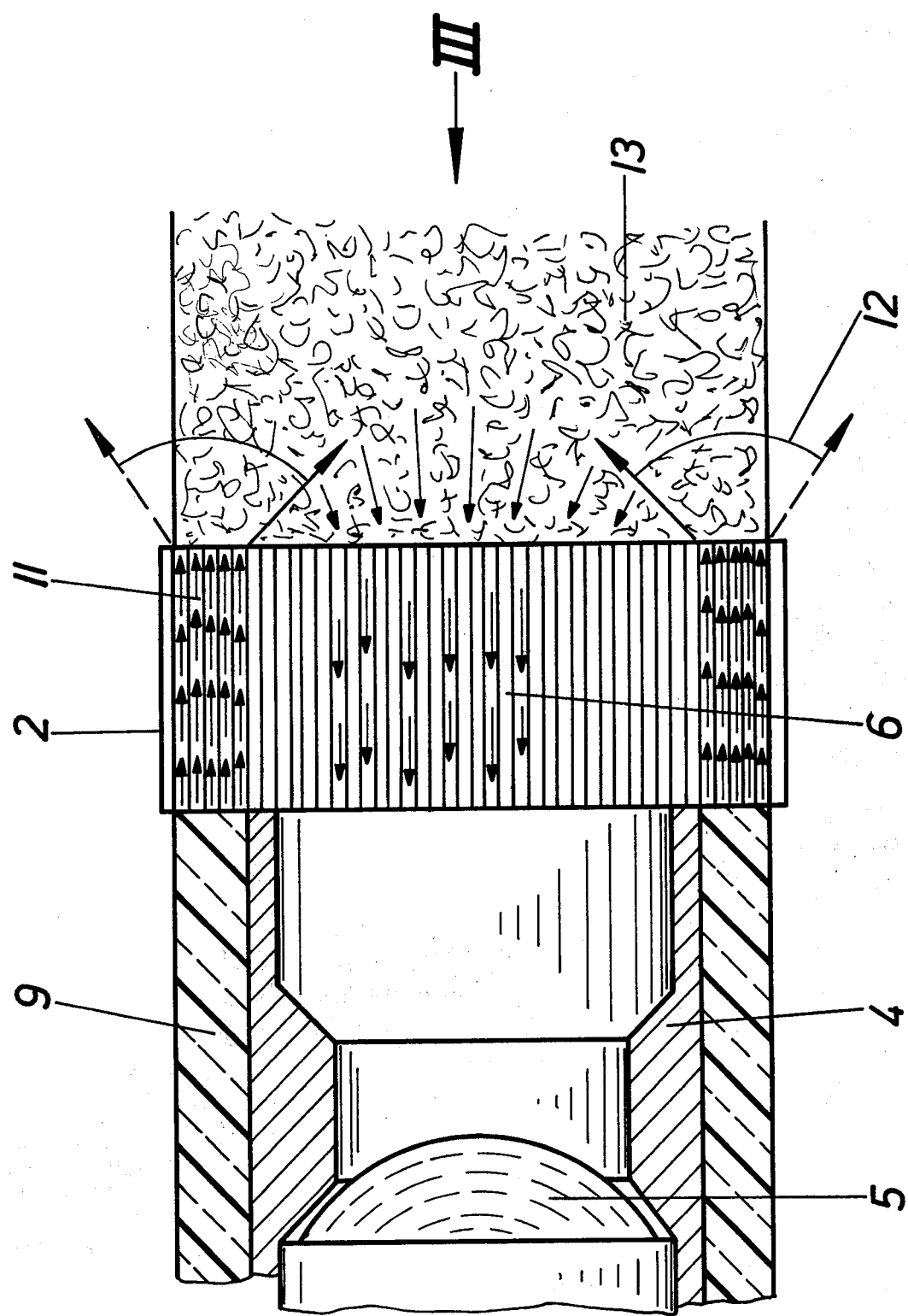
FIG. 2 shows an enlarged partial section through the embodiment shown in FIG. 1.

Referring to the accompanying drawings, a fibre-optical plate 2 is disposed in a housing 1. A seal 3 serves for dust protection. A photo-detector 5, which measures the light incident through the central region of the fibre-optical plate, is arranged in a tube 4 impermeable to light; this central light receiving region being designated by 6 in the FIGS. 2 and 3. Feed means 7 to the photo-detector 5 are conducted through bores 8. The photo-detector 5 and tube 4 are enclosed by a moulded body 9 of acrylic glass which conducts the light radiated by a light-emitting diode 10 to the fibre-optical plate which also has a light exit region designated by 11 in FIGS. 2 and 3.

The light is conducted through the moulded body 9 of acrylic glass and the fibre-optical plate 2 and impinges within a certain opening angle 12 onto the cigarette end 13. Since the tube 4 creates a dark zone of the width of the tube wall between light emitting region 11 and light receiving region 6, the light on its path to the light entry region 6 must traverse at least this path transversely through the cigarette end, i.e. by reflection.

The light intensity measured by the photo-detector 5 is thus a measure of the quantity of light which has passed through the tobacco and thereby a measure of how firmly or loosely the tobacco is packed in the cigarette end.

The co-axial disposition of the light emitting and receiving regions is not the only possible one. As shown in FIG. 4, it is possible for the light emitting region 14 and light receiving region 15 to be rectangular and parallel to each other. It is however essential for the regions to be separated from each other transversely to the axis of the plate 2. This spacing in FIG. 3 is provided by the tube 4 and in FIG. 4 is indicated by A.

The above described device serves for the examination of a single cigarette. In order to examine an entire block of cigarettes at once, an apparatus comprising a plurality of devices may be used, a respective one for each cigarette to be examined. Such an apparatus is shown in FIG. 5. As many devices 18, as there are cigarettes in the block 17 are inserted into a housing 16 and a single common light source comprising a lamp 19 with a parabolic mirror 20 and frosted pane 21, is used.

Since the cigarette end bears directly against the light exit and light entry regions and these are separated by a neutral zone, only such light can reach the receiving surface, which has bridged over the neutral zone transversely to the axis of the cigarette. This occurs through multiple reflection in the interior of the cigarette end, while light in part passes through between the tobacco fibres and in part shines through the tobacco fibres; in this case, the light intensity is strongly reduced. Thus, the more tobacco fibres are present, the weaker is the received signal. When a preset light signal level is now exceeded, the cigarette concerned counts as reject. The capability of resolution of such a device has proved itself to be very good.

I claim:

1. A device for examining the degree of filling of an end zone of a cigarette, comprising a light source, light transmitting means having an emitting surface adapted to be disposed in co-planar relationship to and to be brought into direct contact with an end of said cigarette to be examined and to apply light from said source thereto, light receiving means adapted to be brought into direct contact with the cigarette and having a receiving surface co-planar with said emitting surface and laterally spaced therefrom by a region substantially impermeable to said light, the light being reflected transversely across the end of the cigarette over the impermeable region from the emitting surface to the receiving surface, and evaluating means coupled to said receiving means and responsive to the reflectance of said end zone.

2. A device as defined in claim 1, wherein said emitting surface is co-axial with said receiving surface.

3. A device as defined in claim 1, wherein said emitting surface and said receiving surface are each rectangular and have mutually facing sides extending parallel to each other.

4. A device as defined in claim 1, comprising a fibre-optical member having an end face on which said emitting surface and said receiving surface are provided.

5. A device as defined in claim 4, comprising light conductive means coupling said light source optically to the respective other end face of said fibre-optical member.

6. An apparatus for examining the degree of filling of respective end zone of each of a plurality of cigarettes, comprising a plurality of examining devices, a housing for said devices, and a common light source for said devices, each device comprising light transmitting means having an emitting surface adapted to be disposed in co-planar relationship to and to be brought into direct contact with an end of a respective said cigarette to be examined and to apply light from said source thereto, light receiving means adapted to be brought into direct contact with an end of a respective said cigarette and having a receiving surface co-planar with said emitting surface and laterally spaced therefrom by a region substantially impermeable to said light, the light being reflected traversely across the end of a respective said cigarette over the impermeable region from the emitting surface to the receiving surface, and evaluating means coupled to said receiving means and responsive to the reflectance of said end zone.

* * * * *